United States Patent [19]
Coulter et al.

[11] 3,949,198
[45] Apr. 6, 1976

[54] METHODS AND APPARATUSES FOR CORRECTING COINCIDENCE COUNT INACCURACIES IN A COULTER TYPE OF PARTICLE ANALYZER

[75] Inventors: Wallace H. Coulter, Miami Springs; Walter R. Hogg, Miami Lakes, both of Fla.

[73] Assignee: Coulter Electronics, Inc., Hialeah, Fla.

[22] Filed: Mar. 26, 1974

[21] Appl. No.: 454,793

Related U.S. Application Data

[63] Continuation of Ser. No. 238,079, March 27, 1972, abandoned.

[52] U.S. Cl.......... 235/92 PC; 324/71 CP; 235/92 R
[51] Int. Cl.².................. G01N 27/00; G06M 11/00
[58] Field of Search.......... 235/92 PC, 92 FC, 92 PL

[56] References Cited
UNITED STATES PATENTS
3,444,463  5/1969  Coulter.......................... 235/92 PC Primary Examiner—Joseph M. Thesz, Jr.
Attorney, Agent, or Firm—Silverman & Cass, Ltd.

[57] ABSTRACT

By creating at least two related raw counts $N_1$ and $N_2$, of particles in a fluid suspension either as two physically derived particle counts, or one physical count and an artificial count derived from the physical count, there can be developed a mathematic function relationship by which the "scanning constant" K of a particle analyzer, for example of a Coulter type, can be factored out and a resultant equation obtained. The resultant equation is employable in operating upon the input $N_1$ and $N_2$ raw counts for generating the ultimately desired corrected particle count $N_0$, which eliminates particle coincidence errors. The disclosure encompasses several methods and apparatuses by which the raw counts are developed and by which the related mathematic functions are defined and then employed to obtain corrected counts.

36 Claims, 5 Drawing Figures

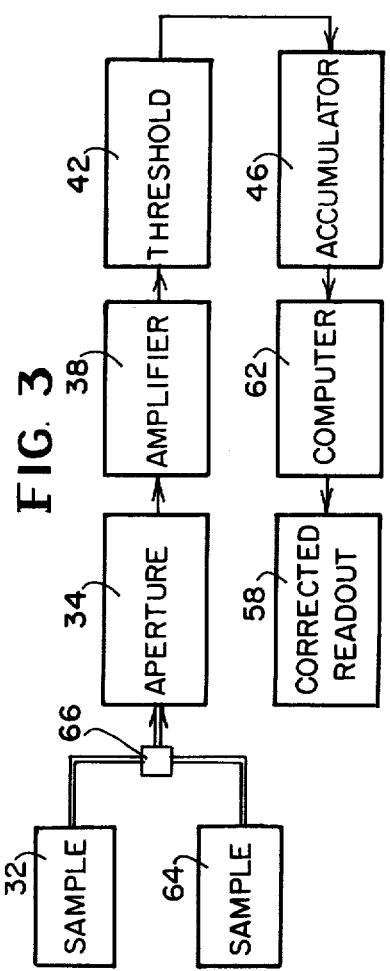
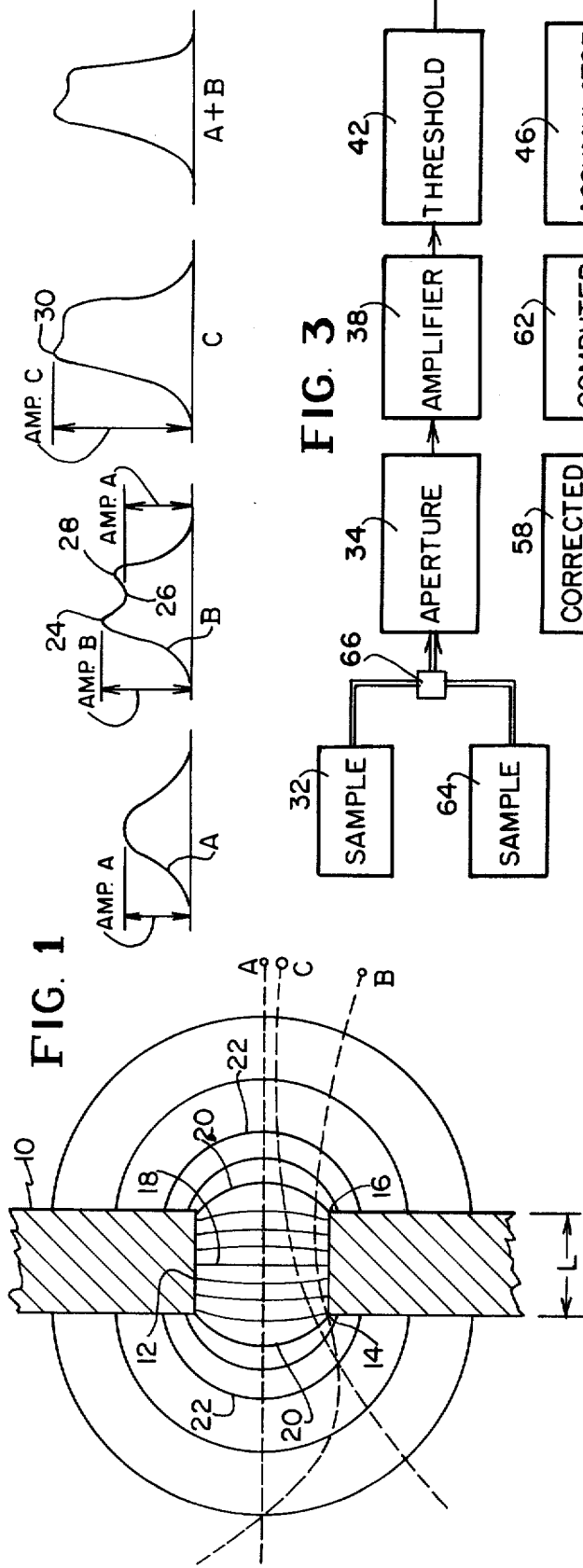
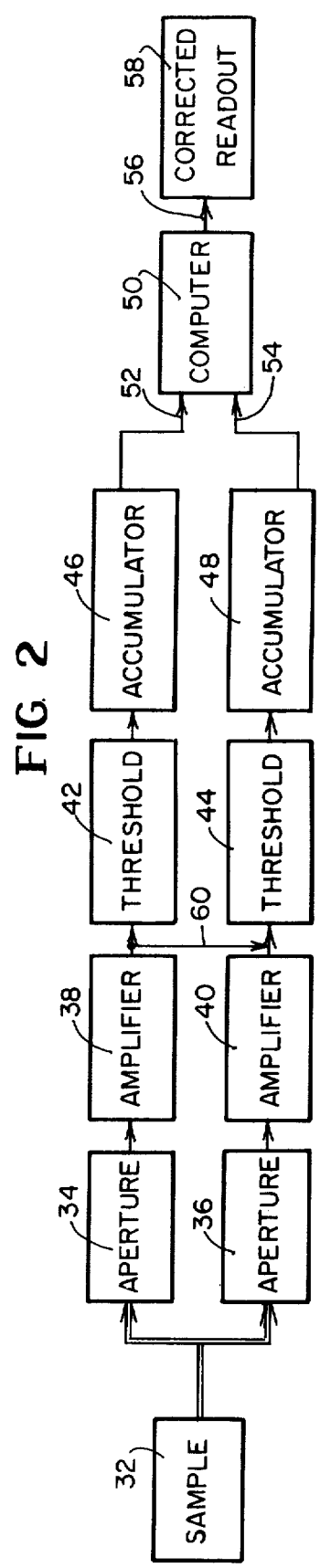

METHODS AND APPARATUSES FOR CORRECTING COINCIDENCE COUNT INACCURACIES IN A COULTER TYPE OF PARTICLE ANALYZER

This is a continuation of application Ser. No. 238,079 filed Mar. 27, 1972, now abandoned.

BACKGROUND OF THE INVENTION

This invention is directed to particle counting methods and apparatuses which provide a statistic correction to a detected train of particle derived count pulses, such that effective random coincidence inaccuracies of count does not induce ultimate counting error.

The particle counting methods and apparatuses concerned employ particle sensing zones in which more than one particle might reside at any one time and thereby randomly generate a coincidence condition. This invention particularly is directed to, but not limited to the determination of nonelectrical properties, such as size and count of microscopic particles, by measuring electrical properties (Patent Office class 324-71NE).

Now well known in the art of electronic particle counting and analyzing is apparatus marketed primarily under the trademark "Coulter Counter". Such apparatus and portions thereof are disclosed in several U.S. patents, for example U.S. Pat. Nos. 2,656,508; 2,985,830; and 3,259,842 (each in class 324-71). A significantly important portion of such Coulter type of apparatus is the minute scanning aperture or scanning ambit or sensing zone relative to or through which pass and are detected single particles at a rate often well in excess of one thousand per second. Because of the physical parameters of the scanning aperture, and particle concentration, there frequently results the coincidence of two particles in the scanning ambit. As a result, there is effectively detected and counted only one particle, not two.

Although such primary form of coincidence loss of count is random in time, it follows a statistically ascertainable form, from which curves, tables, and formulae are obtainable. A relatively simple one of such formulae is: $N' = K N^2$ in which $N'$ = the total number of coincidences, i.e., the required addend; $K$ = a constant which relates primarily to the physical parameters of the scanning elements of the apparatus and $N$ = the detected number of particles, the augend. Accordingly, the true or corrected count $N_O$ will equal the sum of $N+N'$.

Heretofore, the operator of a "Coulter Counter" would obtain the augend count by analysis of a suspension of particles and then would refer to a coincidence correction chart which presented the proper corrected count for a very large selection of augends.

Although the use of charts provides an accurate result, it is both time consuming and prohibits the fully automatic recording and processing of the corrected counts. Also, of course, the accumulating count during analysis is uncorrected. Different charts must be used with apertures of different sizes.

The use of analog, non-linear meters and/or elements in the output stage of a "Coulter Counter" has also been accomplished with limited success; however, in may uses a direct reading digitalized output is greatly to be preferred.

A recently developed, automatic digitalized system and method for coincidence correction, that yields a continuously corrected true count N, is the subject of U.S. Pat. No. 3,626,164. According to the therein described invention, various amounts of the addends are periodically generated by a somewhat complex arrangement of counters and are periodically applied to the continuously accumlating augend count of the particles to yield the true count. Although such method and apparatus provide a distinct advantage over the prior art, they possess the basic limitation of being programmed to a specific correction factor constant K, which itself is tied to the physical parameters of the detecting apparatus, such as the size and volume of the detecting aperture. Hence, changes, such as in aperture size, reqire program changes in the correcting apparatus. Additionally, this somewhat complex arrangement presents a purchase and maintainence cost which must be considered from a commercial sense.

Considerable research effort has been devoted to the phenomena of particle coincidence in a "Coulter Counter". A few of the many publications resulting from such consideration are next listed: Wales, M. and Wilson, J. N., Theory of Coincidence in Particle Counters, *Review of Scient. Instruments*, Vol. 32, Nr. 10, pp. 1132–1136, Oct. 1961; Princen, L. H. and Kwolek, W. F., Coincidence Corrections for Particle Size Determination with the Coulter Counter, *Review of Scientific Instruments*, Vol. 36, Nr. 5, pp. 646–653, May 1965; Strackee, J., Coincidence Loss in Bloodcounters, *Medical and Biological Engineering*, Vol. 4, pp. 97–99, 1966; Princen, L. H., Improved Determination of Calibration and Coincidence Correction Constants for Coulter Counters, *Review of Scient. Instruments*, Vol. 37, Nr. 10, pp. 1416–1418, Oct. 1966; Edmundson, I. C., Coincidence Error in Coulter Counter Particle Size Analysis, *Nature*, Vol. 212, pp. 1450–1452; and Bennert, W. and Hilbig, G., The Theory of the Coincidence Error for Digital Particle Size Analysis, Staub-Reinholt, *Luft*, Vol. 27, Nr. 4, April 1967.

Reduced to its simplest, the count error due to coincidence can be corrected by adding a fraction of the uncorrected or raw count $N_R$. Such fraction can be defined as the "correction factor" $F_C$, for which $$(1) \quad F_c = KN_R,$$

in which K is a very small value "scanning constant". Accordingly, the computation for the true count $N_0$ is:

$$(2) \quad N_0 = (1 + F_c) N_R.$$

Experimentation has shown that the scanning constant K is very nearly the ratio of the critical volume C.V. to the sample volume S; thus, $$(3) \quad K \approx \frac{C.V.}{S},$$

in which the critical volume is that volume defined by the scanning aperture of a Coulter type particle analyzer. Unfortunately, the critical volume is not a fixed amount for any one aperture, and certainly is not the same under varying input conditions. One of the variables that goes into the determination of the critical volume is the electronic field in the immediate vicinity outside of the scanning aperture, which must be included in what has been termed the "scanning ambit" of the particle detector. Such varying electronic field is discussed in U.S. Pat. No. 3,668,531.

Assuming that K is ascertainable, then from equations (1) and (2), $$(4) \quad N_0 = (1 + KN_R) N_R$$

or $$(5) \quad N_0 = N_R + KN_R^2.$$

Unfortunately, due to the extremely small size of most scanning apertures, K has not been easy to isolate with reliability and reproducibility for various input parameters.

Although the Coulter type of particle analyzer, with its aperture form of scanning or sensing zone, is specifically described herein, other forms of particle analyzers, such as those operating with light or acoustic energy and having optical or acoustic sensing zones are encompassed by the invention herein, to the extent that these other types of particle analyzers are subject to particle coincidence in their sensing zones.

SUMMARY OF THE INVENTION

By creating at least two related raw counts $N_1$ and $N_2$, either as two physically derived counts, or one physical count and an artificial count derived from the physical count, there can be developed a mathematic function relationship by which the scanning constant K of a Coulter type of particle analyzer can be factored out and a resultant equation obtained. The resultant equation is employable in operating upon the input $N_1$ and $N_2$ raw counts for generating the ultimately desired corrected count $N_0$.

The invention encompasses method and apparatus by which the raw counts are developed:

a. by passing the sample volume through different scanning apertures having a known difference in their critical volume relationship to obtain $N_1$ and $N_2$;

b. by passing the sample volume through different scanning apertures having the same critical volume and using one output as $N_1$ and the sum of their outputs as $N_2$;

c. by passing two different dilutions of known dilution relationship of the sample through a single scanning aperture to obtain $N_1$ and $N_2$;

d. by passing one sample through one scanning aperture to generate $N_1$ and, by use of delaying and adding $N_1$ to itself, forming $N_2$; and e. by a variation of (d) form a resultant from $N_1$ and $N_2$ which defines the critical volume C.V. rather than the corrected count $N_0$.

BRIEF DESCRIPTION OF THE DRAWING

FIG. 1 is a diagrammatic view illustrating the profile of one form of scanning wafer having particles passing through its aperture along three different paths, with the resulting electric pulses being shown adjacent the aperture profile;

FIG. 2 is a block diagram of coincidence correction apparatus according to two different embodiments of the invention;

FIG. 3 is a block diagram of another embodiment of the invention;

DESCRIPTION OF THE PREFERRED EMBODIMENTS

Figure 4:
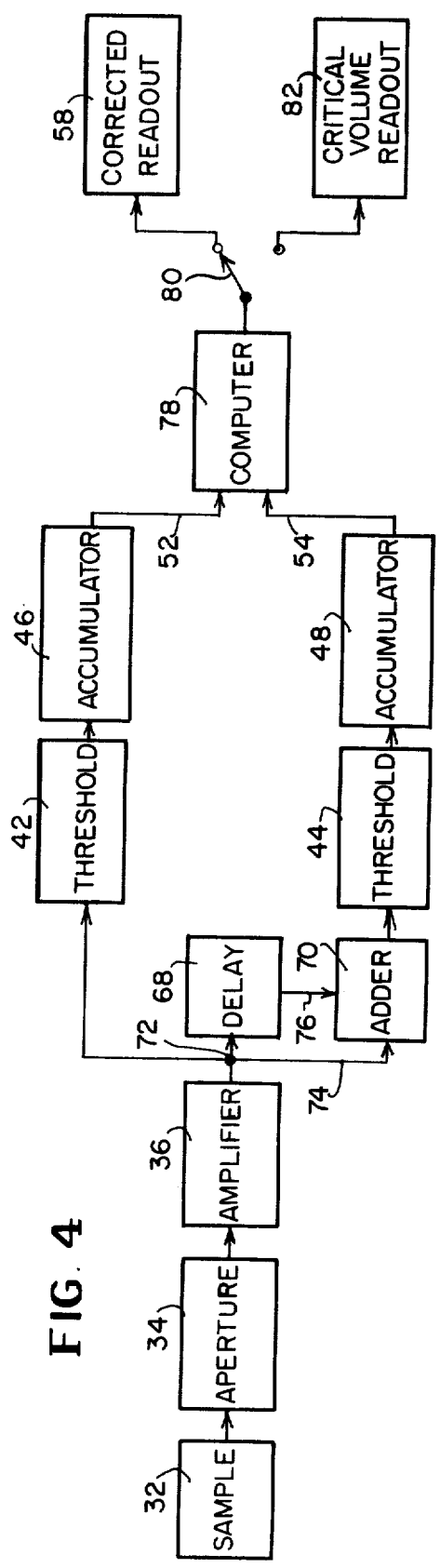
FIG. 4 is a block diagram of a preferred embodiment of the coincidence correction apparatus.

In FIG. 1, there is illustrated the sectional profile of a typical wafer 10 in a "Coulter Counter" counting and sizing apparatus having an aperture 12 therein. The structure is shown simply as a cylindrical bore with sharp edges 14 and 16. When aperture current is established by electrodes (not shown) on oposite sides of the wafer, electricity flows through the aperture from one side to the other, as for example from the left side to the right. The wafer 10 bearing the apparatus 12 is immersed in the sample fluid or electrolyte, but no symbols are used to illustrate this in order to keep the view simple. As the electric current passes through the liquid, the electric current density within and adjacent the aperture is different than it is throughout other parts of the bodies of fluid through which the current passes. In the aperture itself, the electric current density will vary from location to location. The current density at the corners 14 and 16 will be much greater than anywhere else.

Some of the isopotential lines are illustrated in FIG. 1. These lines are shown to be perpendicular at every point where they touch the outer surface of the wafer 10, being transverse of the bore 12 at 18, slightly bulging out at the ends 20, and being quite arcuate at the outer surface of the bulge 22. Taken as a whole, the volume of fluid which is within as well as close to the physical limits of the aperture defines a volume that is effected by the concentration of the degree of density of the electric current so as to define a scanning ambit or critical volume C.V. through which passing particles cause a resistive change and generate detectable pulses. Although the current density in the aperture 12 generally is greater than it is outside of the aperture, the current density is a maximum at the corners 14 and 16, where the electric current turns the corner, so to speak, to enter the aperture 12 and therefore, is greater than in the center of the aperture.

Consider now, three particle paths A, B and C through the aperture from left to right along the broken lines shown in FIG. 1. The first particle A traverses approximately the center of the aperture with the physical stream of liquid and, as it passes from left to right through the influence of the increased current density, its maximum effect upon the resistance of the scanning ambit of the aperture is near the center of the aperture where the isopotential lins 18 are closest and parallel to each other. Considering the graph of the resulting electrical pulse, which may be assumed to have been made by some detecting means as will be discussed with reference to FIGS. 2-4, the pulse is shown as A, its maximum amplitude AMP.A is in its center, and is proportional to the size of the particle A. The duration of the pulse is equal to the time which the particle was within the ambit of the aperture, that is, within its electrical influence. This is considerably more than L, the length of the aperture 12, since, as noted, there is a convex bulge of relatively high electric current density outside of the geometric confines of the aperture.

If all particles follow paths similar to the path A, or quite close to the center of the aperture 12, then all of the resulting pulses would have the appearance of the pulse A, differing only in amplitude, which would be particle size related. It will be appreciated that the dimensions are exaggerated in the view to provide a better understanding of the theory of the discussion. The total duration of the pulse is commonly of the order of 20 to 40 micro-seconds.

All particles do not pass through the aperture 12 along paths similar to path A. Some approach along paths considerably displaced from the axis of the physical stream of liquid and are drawn into the aperture just before the stream enters the entrance to the aperture 12, as the path C, or even closer to the entrance, as the path B. Moreover, more than one particle can reside within and move through the scanning abit at the same time or at least in overlapping times. For purposes of this discussion and the wave forms illustrated in FIG. 1, the particles A and B which traverse the paths A and B are to be assumed to be identical in size; whereas the particle C is twice that size and normally should have an amplitude AMP.C twice that of AMP.A, if it and particle A were to pass along the path A at different times. However, as the particle B moves through the ambient of the aperture 12, it passes close to the corner 14, where the current density is a maximum, and the effect is as though the resitance of the aperture 12 is increased at that point. Accordingly, there will be a peak 24 of amplitude AMP.B at the beginning of the pulse B.

As the particle B enters the aperture 12, it moves into the influence of the electric current region 18, where the density is quite uniform so that the corresponding amplitude of the pulse B will be that of AMP.A as shown in its part 26. As the particle B along the path B leaves the aperture 12, it passes close to the corner 16 through a region of high current density and, therefore, another peak 28 is generated, which would be larger than the part of the pulse indicated at 26.

The particle C, which is twice the size of particle A or B and therefore equal to the sum of their volumes, is shown traversing the path C, which produces the pulse C having a peak amplitude 30 which, while not twice that of the AMP.B of the peak 24 is more than twice AMP.A. The top of the pulse C is neither a smooth curved dome as that of pulse A, nor distinctly dual peaked, as in pulse B, nor are any of the pulses flat topped; hence, there is no single profile which can be used easily to distinguish a particle pulse generated by a single particle from a resulting waveform generated by the coincidence of two or more particles in the aperture ambit. This conclusion holds true, even though the pulse A profile is the most desirable, since coincident derived waveforms can have the profile of pulse A as well as pulse B or C, as next will be detailed with respect to the waveform A+B and also is developed with reference to waveforms in FIG. 5.

If the particles A and B were to traverse the aperture ambit at the same time along their respective paths A and B, there would result the generation of a waveform or pulse A+B as shown in FIG. 1. Such pulse would be the point by point sum of the pulses A and B, as if plotted in a superimposed, well known manner. The striking similarity between the pulse C and the pulse A+B, though somewhat unique, leaves no doubt in the fact that two particles can and do create the electronic pulse image of only one particle even though of different size. Thus, in counting and size distribution studies accomplished by a "Coulter Counter" there will develop a loss of one particle count each time a pulse A+B is generated by the time coincidence of particles in the aperture.

The passage of the particles A and B need not be simultaneous to create a coincidence count loss. If two particles are slightly separated in time, there will be formed a dual peaked pulse, similar to the pulse B. Unfortunately, unless the valley 26 between the peaks 24 and 28 of a profile like pulse B is low enough to cross a low threshold, or the slopes are otherwise distinguishable, pulse analysis is unable to distinguish between a pulse B derived from one or two particles and will report only one particle count; hence, a coincidence loss of one count.

As stated hereinabove, with reference to equations (1) to (4), if the critical volume, C.V., or the scanning constant, K, could be ascertained, then the problem of coincidence errors would be resolved more easily and accurately than heretofor. Such is the goal of the method and apparatus according to FIGS. 2–4, which eliminates K and C.V. as unknowns.

With reference to FIG. 2, consider an arrangement in which a common source of particle sample 32 feeds into two aperture arrangements 34, 36, which respectively, apply their output pulse to amplifiers 38, 40, threshold circuits 42, 44, and accumulators 46, 48. Details of plural aperture setups are disclosed in U.S. Pat. Nos. 3,444,463; 3,444,464; and 3,549,994 (class 324-71). It is to be assumed that the "aperture" blocks contain not only the aperture wafer 10 and aperture 12, but also the aperture tubes, beakers, sample moving and measuring structures, electrodes, etc., all well known and disclosed in the patents cited herein.

If the particle analyzer is other than of the Coulter type, the blocks 34 and 36 will contain their appropriate sensing zone arrangements. Hence, the term "aperture" as used herein is not limiting.

For the first embodiment of the invention, both method and apparatus, consider the sensing zones or apertures in the blocks 34 and 36 of FIG. 2 to be of different volumes, and with the "aperture" of 36 to be twice the critical volume of the "aperture" of 34. By substitution into equation (4):

$$(6) \; N_0 = (1 + K_1 N_1) N_1$$

and $$(7) \; N_0 = (1 + K_2 N_2) N_2.$$

wherein the uncorrected or raw count $N_R$ from the apertures 34 and 36 are, respectively $N_1$ and $N_2$, and their scanning constants are $K_1$ and $K_2$, respectively. Since we have chosen the ratio of their aperture volumes to be 1:2, for example, then $2K_1 = K_2$. By substitution into (6) and (7):

$$(8) \; N_0 (1 + K_1 N_1) N_1$$

and $$(9) \; N_0 = (1 + 2K_1 N_2) N_2;$$

and by solving these simultaneous equations for $K_1$, $$(10) \quad K_1 = \frac{N_0 - N_1}{N_1^2} \text{ and } K_1 = \frac{N_0 - N_2}{2N_2^2};$$

hence, $$(11) \quad \frac{N_0 - N_1}{N_1^2} = \frac{N_0 - N_2}{2 N_2^2}.$$

Next, by solving for $N_0$, this true count can be expressed in terms of the two raw counts $N_1$ and $N_2$:

$$(12) \quad N_0 = \frac{2 N_1 N_2^2 - N_2 N_1^2}{2 N_2^2 - N_1^2} = N_1 N_2 \frac{2 N_2 - N_1}{2 N_2^2 - N_1^2}.$$

Although equation (12) is a rather complex expression, it does not contain any constants of calibration nor does it depend upon knowledge of the critical volume per se and thereby it meets the basic needs and principles of the invention. Moreover, such mathematic function can be built int a computation unit, such as represented by a computer block 50 in FIG. 2, which receives the raw counts $N_1$ and $N_2$ at inputs 52 and 54 from the accumulators 46 and 48, to provide from its output 56 a coincidence corrected count for receipt by any one or more of known readout devices, represented by a corrected readout device 58.

The computational unit 50 in FIG. 2 as well as the "computer" blocks in FIGS. 3 and 4 can be any of many well known general purpose computers which can be connected to the accumulators, or even can include the accumulator stages. The programmed data processor line of minicomputers by Digital Equipment Corporation has been employed successfully for receiving and processing data from various Coulter Counter particle analyzers. A PDP-8E minicomputer can meet the needs of the computational processng hereinafter set forth. Of course, computation can be accomplshed by pencil and paper as well as by a hand-operated calculator.

It will be appreciated that the volume ratio determines the numeric multipliers in equation (12). If, for example, the ratio was 1:5 rather than 1:2, the multiplier 5 would replace the value of 2 in all instances.

Notwithstanding the fact that the apertures 34 and 36 have two different critical volumes, the same amount of sample is to flow through each; hence, the true count of the particles passing therethrough should be the same for each aperture, were it not for the coincidence phenomena, which operates differently upon the apertures because of their differences in C.V. and K.

A variation of the just described embodiment involves almost the same arrangement, except for the fact that the apertures in the blocks 34 and 36 are to have the same critical volumes and there is added an input line 60 from the output of one amplifier 38 to the input of the other threshold 44. As illustrated the accumulator 48 thereby will apply onto its output line 54 the sum of the particle pulses transduced by both apertures 46 and 48, such sum being $N_2$. By employing equation (251 presented subsequently, $N_0$ can be derived for this arrangement.

In the two embodiments described with reference to FIG. 2, there is the assumption that apertures having known relationships with respect to their critical volumes are obtainable; whereas, it is also a basic premise of the problem that the actual volume, and therefor the critical volume of an aperture is not ascertainable. The named assumption is not rendered impossible or even impractical by the named premise, since one does not have to ascertain the actual volumes to be able to empirically construct two apertures having a known ratio of their (unknown) volumes. Nevertheless, the use of two apertures and two parallel channels of components presents cost, space, maintenance and other considerations which would be reduced if only one aperture was needed. Such is accomplished in the next described embodiments of FIGS. 3 and 4.

With reference to FIG. 3, the aperture 34, amplifier 38, threshold circuit 42, accumulator 46 and readout device 58 can be the same as those same named elements of FIG. 2. A computer 62 can be the same basic structure as that of the computer 50; however, it will be programmed to a different mathematic function, which is next described, and it receives only one raw count at any one time. The sample input arrangement provides for two different dilutions of the same sample and of a known dilution ratio. The two dilutions only are diagrammatically shown in two containers 32 and 64 and their method of formation can be by any manner by which their relative dilutions can be ascertained. For example, the sample 32 can be analyzed and returned to the "container" 32 and there be diluted to become the sample 64.

For the description herein, it is assumed that the sample dilutions are 1:2, with the sample 64 that produces the raw count $N_2$ having been diluted by a factor of 2 from the sample 32 producing the raw count $N_1$. Suitable fluid flow control means 66 will determine which sample is being received by the aperture at any time and will ensure that equal amounts of the samples flow.

Since the same aperture is employed for both dilutions, the same scanning constant, $K$, is found in equations (13) through (18). Also, since the true count $N_0$ with respect to the sample 64 will be halved by the act of diluting the sample 64, the term $N_0/2$ will be employed in equation (14). For convenience, let $J = N_1/N_2$.

$$(13) \quad N_0 = (1 + K N_1) N_1.$$

and $$(14) \quad N_0/2 = (1 + K N_2) N_2;$$

therefore, by substitution $$(15) \quad N_0 = J N_2 + K J^2 N_2^2$$

and $$(16) \quad J^2 N_0/2 = J^2 N_2 + J^2 K N_2^2.$$

By subtraction of (16) from (15) and solving for $N_0$:

$$(17) \quad N_0 = 2 J N_2 \frac{J-1}{J^2 - 2}.$$

and by substitution of $N_1/N_2$ for $J$;

$$(18) \quad N_0 = 2 N_1 N_2 \frac{N_1 - N_2}{N_1^2 - 2 N_2^2}.$$

which is the mathematic function built into the computer 62.

It is believed that the operation of the FIG. 3 apparatus and the method thereof is evident from the foregoing. The multiplier in equation (18) is determined by the dilution ratio, such that the digit value 2 (both occurrences) would become 5 if the sample 64 was a 1:5 dilution.

Although the FIG. 3 embodiment is an improvement over the FIG. 2 embodiments, as earlier discussed, it possesses certain drawbacks. If the time and equipment necessary for making two precise dilutions and passing equal amounts of sample, and the time for processing the two dilutions sequentially could be eliminated there would be provided yet another significant improvement over the basic invention; such is accomplished by the embodiment of FIG. 4, in which the components having the same reference numbers as those in FIG. 2 can be employed.

The process of the FIG. 4 embodiment operates upon the premise that a single sample 32 passing through only one aperture 34 can provide both of the raw counts $N_1$ and $N_2$. To accomplish such goal, one of the raw counts, $N_2$, is created artifically from the same particle pulse train that generates the count $N_1$. By using the same particle pulses for both $N_1$ and $N_2$, there will be less random variations than if two apertures or two samples are employed. Effectively, the counts $N_1$ and $N_2$ represent two known dilutions with the stronger dilution being synthesized from the weaker dilution by an electronic delay device 68 and an adder circuit 70 being interposed between the aperture 34 and one accumulator 48 of the two parallel channel coupled accumulators.

Figure 5:
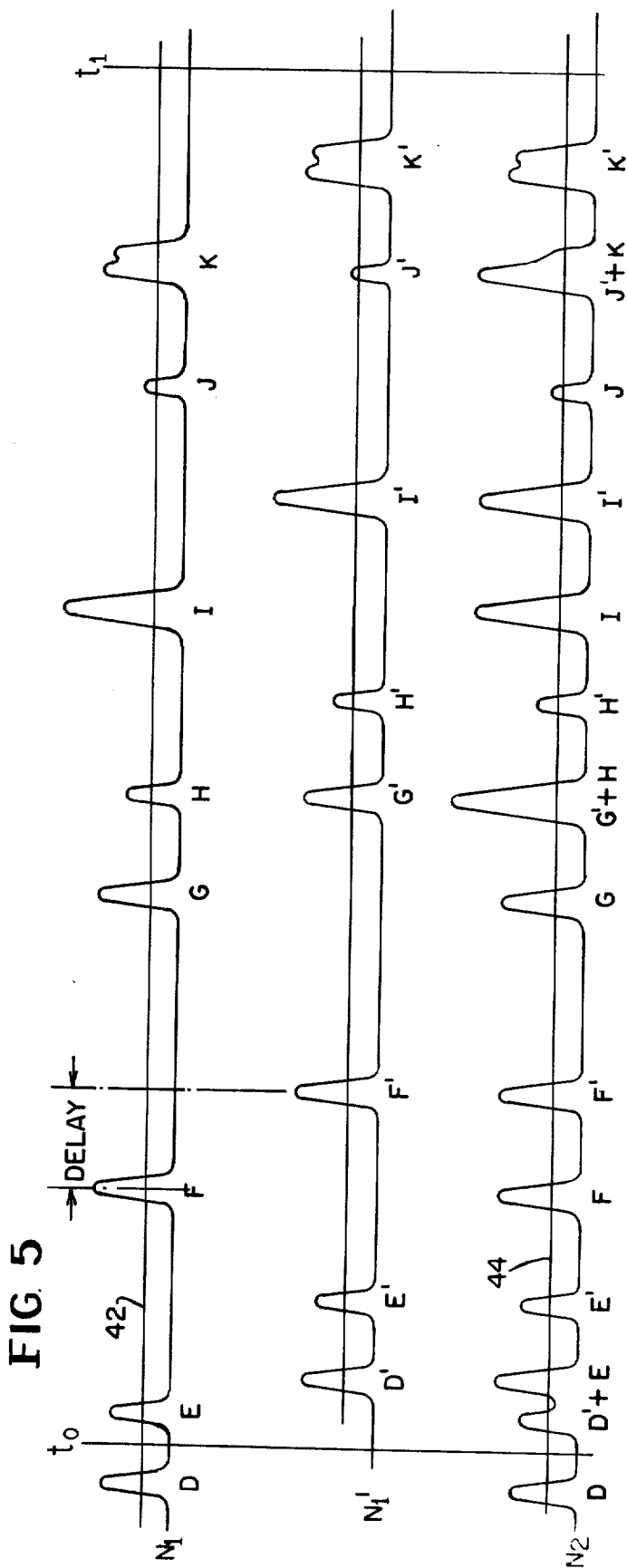
FIG. 5 is a plurality of graphs of representative particle pulses, for illustration of the invention according to the apparatus of FIG. 4.

As shown in FIGS. 4 and 5, output train $N_1$ of particle pulses D through K from the Coulter type aperture 34 is fed through the amplifier 36 to a junction point 72, from whence the entire train of particle pulses is applied on three separate paths to the threshold circuit 42, to the delay device 68, and directly to the adder circuit 70, the latter by an input line 74. The delayed train $N_1'$ of pulses D' through K' is applied from the delay circuit to the adder circuit by a line 76. The amount of delay is shown in FIG. 5 with reference to the time between the pulses F and F'. The delay duration can be arbitrarily chosen at almost any value greater than that which itself would create a coincidence error between a pulse and its own delayed counterpart.

Looking first at the train of pulses $N_1$, for simplicity all are shown to exceed the low threshold level 42 and thus are assumed to originate from particles of interest to the accumulator 46. However, the twin peaked pulse K appears to represent the not quite simultaneous passage of two particles and the large amplitude pulse I might represent the simultaneous passage of two small particles through the aperture 34. As shown, with respect to the pulse train $N_2$, the addition of $N_1$ and $N_1'$ forms the individual and unaltered pulses D, E', F, F', G, H', I, I', J, and K, as well as the "combined" pulses D' + E, G' + H, and J' + K, each of which can be accumulated as a single particle pulse when its trailing edge crosses the threshold 44. Hence pulses D' and E can be counted separately; whereas, the pulses G' + H and J' + K produce coincidence lost counts, with the pulse J' K probably being a synthetic triplet, i.e., two lost counts. The fact that the random spacing between pulses G and H equaled the delay time, caused the sum of G' and H to form a simultaneous coincidence pulse G' + H situation, like that of the pulse A + B in FIG. 1. In this manner, the accumulators 46 and 48 will register respectively $N_1 = 7$ and $N_2 = 13$ and fed them into the computer 78.

The computer 78 can be the same as the computer 50 and will receive $N_1$ as an input on the line 52 and $N_2$ on the line 54. The computation factor or function programmed into the computer 78 is developed as follows, with $2N_0$ representing the synthesized double concentration count $N_2$ if coincidence corrected itself, and $J = N_2/N_1$.

(19) $N_0 = (1 + K N_1) N_1 = N_1 + K N_1^2$ and

(20) $2N_0 = (1 + K N_2) N_2 = N_2 + K N_2^2$.

By multplying (19) by $J^2$ and (20) by $N_1/N_1$ and $N_1^2/N_1^2$, K can be factored out as follows:

(21) $J^2 N_0 = J^2 N_1 + J^2 N_1^2 K$ and

(22) $2N_0 = J N_1 + J^2 N_1^2 K$;

subtracting (22) from (21), and dividing by J,

(23) $J N_0 - \dfrac{2N_0}{J} = J N_1 - N_1$;

whereupon solving for $N_0$,

(24) $N_0 = \dfrac{J N_1 - N_1}{J - \dfrac{2}{J}} = J N_1 \dfrac{J - 1}{J^2 - 2}$;

and substituting $N_2/N_1 = J$,

(25) $\dfrac{N_2}{N_1} \cdot N_1 \cdot \dfrac{\dfrac{N_2}{N_1} - \dfrac{N_1}{N_1}}{\dfrac{N_2^2}{N_1^2} - 2 \dfrac{N_1^2}{N_1^2}} = N_1 N_2 \dfrac{N_2 - N_1}{N_2^2 - 2N_1^2}$ Although the pulse trains $N_1$ and $N_2$ do not possess enough pulses for a meaningful analysis and derivation of their corrected count $N_0$, the formula (25) will be applied for the time interval of $t_0$ to $t_1$ with the value of $N_1 = 7$ and $N_2 = 13$ $N_0 = (13)(7) \dfrac{13 - 7}{169 - 98} = 91 \dfrac{6}{\phantom{169-98}} = 7.85.$ Assuming that the pulse I was caused by only one particle, but that the pulse K was caused by the coincidence of two particles, the actual number of processed particles was 8 and the derived $N_0$ is only 2% different from the true count, an especially close answer for a calculation based upon only seven events. It will be appreciated that in the normal operation of a Coulter Counter, several thousand particles can be processed in one second; hence, the counts $N_1$ and $N_2$ will be quite large, even in a very short duration of $t_0$ to $t_1$.

In addition to or in lieu of coupling the computer 78 to the corrected readout element 58, as shown by way of a switch 80, the computer can be programmed with a second function

(26) $C.V. = S \dfrac{2N_1 - N_2}{N_1^2}$ from which the critical volume can be derived. Such output is diagrammatically shown in FIG. 4 as being capable of being fed from the computer 78 through the switch 80 into a critical volume readout device 82. As diagrammatically suggested, the position of the switch 80 could determine which computer operation (25) or (26) is being accomplished at any one time. Of course, both functions could be programmed for simultaneous readout of $N_0$ and C.V.

Since the arrangement of FIG. 4 can be employed for ascertaining the critical volume, the hereinabove discussed problems related to C.V. can be reduced and the production and utilization controls over the aperture per se can be improved.

The derivation of equation (26) is set forth below, with equation (27) being traceable to equation (1) of Grant, Britton, and Kurtz, "Measurement of Red Cell Volume with the Electronic Cell Counter", *American Journal of Clinical Pathology*, February, 1960, Vol. 33, No. 2, pp. 138–143.

$$(27)\ N_0 = -1/d\ \ln(1 - d\,N_1).$$

in which $d = $ C.V./S, S being the total volume of the sample that is analyzed; then, $$(28)\ 2N_0 = -1/d\ \ln(1 - d\,N_2).$$

By multiplying both sides of equations (27) and (28) by $-d$ and then raising $e$ to the power of each equation, the logarithmic expression can be eliminated to yield $$(29)\ e^{-d N_0} = 1 - d\,N_1$$

and $$(30)\ e^{-2d N_0} = 1 - d\,N_2.$$

Upon dividing (29) by (30) and simplifying, $$(31)\quad e^{d N_0} = \frac{1 - d\,N_1}{1 - d\,N_2}.$$

It is to be noted that the reciprocal of equation (29) is $$e^{d N_0} = \frac{1}{1 - d\,N_1}$$

which can be substituted into equation (31) to obtain $$(32)\quad \frac{1}{1 - d\,N_1} = \frac{1 - d\,N_1}{1 - d\,N_2}.$$

Thereupon, by multiplying means by extremes expanding, dividing by $d$ and solving for $d$, one obtains $$(33)\quad d = \frac{2 N_1 - N_2}{N_1^2}.$$

Since by definition $$d = \frac{C.V.}{S}.$$

equation (26) results.

Although several specific formulas for $N_0$ and C.V. have been presented hereinabove for various $N_1$ and $N_2$ origins and relationships, such formulas being programmed into the computers in FIGS. 2–4, it is possible that other equally valid formulas for $N_0$ and/or C.V. can be developed and then be applied with satisfactory results according to the methods and apparatus of the invention claimed herein. Accordingly, the specific formulas are only examples of a broader or generic group of mathematic function relationships between $N_1$ and $N_2$ which can be employed within the scope of the invention.

Furthermore, it will be recognized by those skilled in the art that, although the invention is described in connection with the Coulter type of particle analyzer, it will apply equally well to any particle-counting apparatus which employs a sensing zone, whether this sensing zone is energized by an electric field, as in the "Coulter Counter", or by light, acoustic energy, or a magnetic field.

What is sought to be claimed and protected by United States Letters Patent is:

1. A method for use in the automatic correction of coincident particle count inaccuracies in a particle analyzer of the sensing zone type comprising the steps of: generating a first and a second train of particle pulses by passing at least one portion of a sample of particles through at least one sensing zone type of particle sensing zone arrangement, said step of generating the pulse trains including the step of establishing at least one of them in such a manner to have a different number of pulses than the other by use of a ratio, other than unity, of at least one of sample dilutions, sample volumes, and sensing zone volumes with respect to the establishing of the other pulse train, that the number of pulses in the first train is in accordance with a coincidence count interrelated mathematic function relationship with respect to the number of pulses in the second train, in which the only unknowns in such relationship are the number of pulses in each train; the number of pulses in each train and said ratios being all of the mathematic factors required in the solving of a specific coincidence correction equation for a resultant coincidence corrected particle count.

2. The method according to claim 1, in which said step of establishing includes the passing of equal volumes of particle sample separately through two sensing zones the critical volumes of which having a known ratio, and arranging pulse count accumulating of the trains of pulses such that the pulse count of one train comes solely from one sensing zone and the pulse count of the other train comes at least in part from all of the train associated with the other sensing zone.

3. The method according to claim 2 in which said step of establishing includes transducing the particles by sensing zones having unequal critical volumes, and arranging both train pulse counts to be accumulated exclusively and separately from each separate sensing zone.

4. The method according to claim 2 in which said step of establishing includes transducing the particles into pulses by sensing zones having equal critical volumes, arranging said accumulating such that the arithmetic sum of pulses of both trains is accumulated along with the pulse count of one of the trains.

5. The method according to claim 2 in which said steps include mathematically employing the function $$N_0 = N_1 N_2 \frac{2 N_2 - N_1}{2 N_2^2 - N_1^2}.$$

in which:

$N_0$ is the corrected count,
$N_1$ is the pulse count of said first train, and
$N_2$ is the pulse count of said second train.

6. The method according to claim 1 in which said step of establishing includes the forming of two different dilutions of known dilution ratio of the particle sample and of the same volume, and passing such dilutions separately through a single sensing zone to separately develop the pulse trains for separate accumulating of their pulse counts.

7. The method according to claim 6 in which said steps include mathematically employing the function $$N_0 = 2 N_1 N_2 \frac{N_1 - N_2}{N_1^2 - 2 N_2^2}.$$

in which:

$N_0$ is the corrected count;
$N_1$ is the pulse count of said first train, and
$N_2$ is the pulse count of said second train.

8. The method according to claim 1 in which said step of establishing includes the passing of the entire particle sample through a single sensing zone for generating one of the trains of particle pulses, and artifically creating from that one train the other of the trains of pulses for their separate accumulating.

9. The method according to claim 8 in which said artifically creating is accomplished by adding the one pulse train pulses themselves, not their counts, to that same pulse train pulses themselves which have been delayed.

10. The method according to claim 9 in which said steps include mathematically employing the function $$N_0 = N_1 N_2 \frac{N_2 - N_1}{N_2^2 - 2 N_1^2}.$$

in which:

$N_0$ is the correct count,
$N_1$ is the pulse count of said first train, and
$N_2$ is the pulse count of said second train.

11. The method according to claim 8 which further comprises the step of mathematically employing both of the accumulated counts to solve an equation in terms of the critical volume of the sensing zone and deriving as a resultant the critical volume.

12. The method according to claim 11 in which said artificially creating is accomplished by adding the one pulse train pulses themselves, not their counts, to that same pulse train pulses themselves which have been delayed.

13. The method according to claim 11 in which said step of mathematically employing encompasses the function $$C.V. = S \frac{2 N_1 - N_2}{N_1^2}.$$

in which:

$C.V.$ is the critical volume,
$S$ is the total volume of analyzed sample,
$N_1$ is the pulse count of said first train, and
$N_2$ is the pulse count of said second train.

14. A method for use in the automatic determination of the critical volume of the sensing zone in a particle analyzer of the sensing zone type whereby coincident particle count inaccuracies therein can be ascertained, comprising the steps of: generating a first and a second train of particle pulses by passing a sample of particles through the sensing zone of the particle analyzer, said step of generating the pulse trains including the step of establishing at least one of them with reference to the other train and the volume of the sample in such a manner that the number of pulses in each train are different from each other and are in accordance with an interrelated mathematic function relationship with respect to sensing zone critical volume, in which the only unknowns in such relationship are the number of pulses in each train, said step of establishing including artificially creating from said first train said second train of pulses; the number of pulses in each train and the sample volume being all of the mathematic factors required in the solving of a specific critical volume equation for the sensing zone critical volume.

15. The method according to claim 14 in which said artificially creating is accomplished by adding the first pulse train pulses themselves, not their counts, to that same pulse train pulses themselves which have been delayed by virture of affixing a quantum of delay to the first pulse train.

16. The method according to claim 15 in which said steps include mathematically employing the function $$C.V. = S \frac{2N_1 - N_2}{N_1^2},$$

in which:

$C.V.$ is the critical volume,
$S$ is the total volume of analyzed sample,
$N_1$ is the pulse count of said first train, and
$N_2$ is the pulse count of said second train.

17. Apparatus for use in the automatic correction of coincident particle count inaccuracies in a particle analyzer of the sensing zone type, comprising: means for genrating a first and a second train of particle pulses, said generating means including at least one sensing zone arrangement and means for supplying at least one portion of a sample of particles for passage through the sensing zone arrangement for the development of pulses from each of the pulse trains; said generating means further including control means interconnecting said sensing zone arrangement and said supplying means for controlling sample passage and particle pulse generating; said supply means, sensing zone arrangement, and control means being intercoupled for establishing at least one of a ratio, other than unity, of sample dilutions, sample volumes, and sensing zone volumes such that the pulse development results in a different number of pulses in each train and the trains possess a coincidence count interrelated mathematic function relationship with respect to the number of pulses in each train pertaining to their coincidence corrected true count in terms exclusive of any other unknowns; and the number of pulses in each train along with the employed ratios provide all of the mathematic factors required in the solving of a specific coincidence correction equation for a resultant coincidence corrected particle count.

18. The apparatus according to claim 17 including accumulator means for pulse count accumulating separately the pulses from each of the pulse trains as two output count signals in which said generating means includes a supply of the sample wherein the improvement comprises: two sensing zones, the critical volumes of which are of a known ratio, said generating means being constructed and arranged with respect to said controlling means for the passing of equal volumes of the particle sample separately through said two sensing zones, and determining the mode of accumulating by said accumulator means, such that the pulse count of one train comes solely from one said sensing zone and the pulse count of the other train comes at least in part from all of the train associated with the other said sensing zone.

19. The apparatus according to claim 18 in which said sensing zones have unequal critical volumes, and said controlling means and said accumulator means are interconnected such that both train pulse counts from each separate zone are accumulated exclusively and separately.

20. The apparatus according to claim 18 in which said sensing zones have equal critical volumes, said controlling means and said accumulator means are interconnected such that the arithmetic sum of pulses of both trains is accumulated to define one of the two said output count signals and the pulse count of one of the trains is accumulated to define the other of said output count signals.

21. The apparatus according to claim 18 in which computation means is provided to perform the coincidence correction mathematic operation $$N_0 = N_1 N_2 \frac{2 N_2 - N_1}{2 N_2^2 - N_1^2},$$

in which said two output count signals are $N_1$ and $N_2$.

22. The apparatus according to claim 17 including accumulator means for pulse count accumulating separately the pulses from each of the pulse trains as two output count signals in which said sensing zone arrangement has only a single sensing zone, wherein the improvement comprises: said supplying means includes means for the forming of two different dilutions of known dilution ratio of the particle sample and of the same volume for the passing of such dilutions separately through the single sensing zone, to separately develop the pulse trains for the separate accumulating by said accumulator means.

23. The apparatus according to claim 22 in which computation means is provided to perform the mathematic operation $$N_0 = 2 N_1 N_2 \frac{N_1 - N_2}{N_1^2 - 2 N_2^2},$$

in which:
$N_0$ is the coincidence corrected count,
$N_1$ is the pulse count of said first train, and
$N_2$ is the pulse count of said second train.

24. The apparatus according to claim 17 including accumulator means for pulse count accumulating separately the pulses from each of the pulse trains as two output count signals in which said sensing zone arrangement and said supplying means provide for the passing of the entire particle sample through a single sensing zone for generating one of the trains of particle pulses, wherein the improvement comprises: said controlling means includes electronic structure for artificially creating from that one train the other of the trains of pulses for their separate pulse count accumulating.

25. Apparatus according to claim 24 in which said electronic structure includes the combination of pulse delay means and pulse waveform adding means interposed between said sensing arrangement and said accumulator means and intercoupled to define one of said output signals by adding the one pulse train pulse waveforms, to the same waveforms which have been delayed.

26. The apparatus according to claim 25 in which said computation means is constructed to perform the mathematic operation $$N_0 = N_1 N_2 \frac{N_2 - N_1}{N_2^2 - 2 N_1^2},$$

in which:
$N_0$ is the corrected count,
$N_1$ is the pulse count of said first train, and
$N_2$ is the pulse count of said second train.

27. The apparatus according to claim 24 in which computation means further is provided for mathematically operating upon both of the accumulated pulse counts to solve an equation in terms of the critical volume of the sensing zone and thereby for deriving as a resultant the critical volume.

28. Apparatus according to claim 27 in which said electronic structure includes the combination of pulse delay means and pulse waveform adding means interposed between said sensing arrangement and said accumulator means and intercoupled to define one of said output signals by adding the one pulse train pulse waveforms, not their counts, to the same waveforms which have been delayed.

29. The apparatus according to claim 27 in which said computation means is constructed to perform the mathematic operation $$C.V. = S \frac{2 N_1 - N_2}{N_1^2},$$

in which:
$C.V.$ is the critical volume,
$S$ is the total volume of analyzed sample,
$N_1$ is the pulse count of said first train, and
$N_2$ is the pulse count of said second train.

30. Apparatus for use in the automatic determination of the critical volume of the sensing zone in a particle analyzer with a sensing zone, comprising: means for generating a first and a second train of particle pulses, said generating means including one sensing zone arrangement and means for supplying a sample of particles for passage through the sensing zone arrangement for the development of the pulse trains; said generating means further including control means connected to said sensing zone arrangement for controlling particle pulse generating by artificially creating from said first train said second train of pulses; said supply means, sensing zone arrangement, and control means being intercoupled for generating the trains of pulses relative to each other such that the pulse development possesses an interrelated mathematic function relationship with respect to the number of pulses in each train pertaining to the critical volume of the sensing zone in terms exclusive of any other unknowns; and the number of pulses in each train along with the sample volume provide all of the mathematic factors required in the solving of a specific critical volume equation for the sensing zone critical volume.

31. Apparatus according to claim 30 including accumulator means for pulse count accumulating separately the pulses from each of the pulse trains as two output count signals, wherein the improvement comprises: said control means includes the combination of pulse delay means and pulse waveform adding means interposed between said sensing zone arrangement and said accumulator means and intercoupled to define one of said output signals by adding the one pulse train pulse waveforms, not their counts, to the same waveforms which have been delayed.

32. The apparatus according to claim 31 in which computation means is provided to perform the mathematic operation $$C.V. = S \frac{2 N_1 - N_2}{N_1^2}.$$

in which:
C.v. is the critical volume,
S is the total volume of analyzed sample,
$N_1$ is the pulse count of said first train, and
$N_2$ is the pulse count of said second train.

33. Apparatus according to claim 30 in which said sensing zone is a Coulter-type scanning aperture.

34. Apparatus according to claim 17 in which said sensing zone is a Coulter-type scanning aperture.

35. In the analysis of particles by a particle analyzer of the sensing zone type, a method for simulating a particulate sample having a size distribution and concentration related to a test sample, comprising the steps of: passing a test sample of particles through the sensing zone of an electronic particle analyzer; generating, by said passing, a first train of electrical pulses, each pulse of said first train normally representing one particle of the test sample; deriving electronically from said first train a time-delayed equivalent train of pulses; adding electronically in a pulse-by-pulse manner said first train and said equivalent train and thereby forming a second pulse train, said second pulse train being a simulated representation of a train of pulses generated from a sensing zone, through which has passed a particulate sample having twice the concentration and substantially the same size distribution as the test sample.

36. For the analysis of particles by a particle analyzer of the sensing zone type, apparatus for simulating a particulate sample having a distribution and concentration related to a test sample, said apparatus comprising: a sensing zone arrangement and means for supplying at least a portion of a test sample of particles for passage through the sensing zone arrangement; means for generating, by said particle passage, a first train of electrical pulses, each pulse of said first train normally representing one of the passed particles; means for deriving electronically from said first pulse train a time-delayed equivalent train of particle pulses; pulse wave form adding means for adding electronically in a pulse-by-pulse manner said first train and said equivalent train and thereby forming a second pulse train, said second pulse train being a simulated representation of a train of pulses generated from a sensing zone, through which has passed a particulate sample having twice the concentration and substantially the same size distribution as the test sample.

* * * * *

UNITED STATES PATENT AND TRADEMARK OFFICE
CERTIFICATE OF CORRECTION

PATENT NO. : 3,949,198
DATED : April 6, 1976
INVENTOR(S) : Wallace H. Coulter, et al It is certified that error appears in the above-identified patent and that said Letters Patent are hereby corrected as shown below:

Column 1, line 65, change "may" to -- many --. Column 2, line 14, change "rqire" to -- require --. Column 4, line 52, change "lins" to -- lines --. Column 5, line 13, change "abit" to -- ambit--; line 22, change "ambient" to -- ambit --. Column 6, line 24, change "pulse" to -- pulses --; line 29, after "assumed" insert -- herein --. Column 7, line 17, change "int" to -- into --; column 7, line 40, put quotes around "5"; line 40, put quotes around "2"; column 7, line 57, change "(251" to -- (25) --. Column 8, line 68, put quotes around "2". Column 9, line 1, put quotes around "5". Column 10, line 14, change "multplying" to -- multiplying --; column 10, line 50, change "6" to read -- $\frac{6}{71}$ --. Column 11, line 56, after "extremes" insert a comma.
Column 13, line 32, change "artifically" to -- artificially --.
Column 14, line 47, change "genrating" to -- generating --.
Column 16, line 15, after "wafeforms" insert --,not their counts,-- column 16, line 18 delete "said", change "constructed" to -- provided --; line 26 after "the" insert -- coincidence --.
Column 17, line 30, change "v" to -- V --.

Signed and Sealed this

Ninth Day of November 1976

[SEAL]

Attest:

RUTH C. MASON
Attesting Officer

C. MARSHALL DANN
Commissioner of Patents and Trademarks